Nov. 23, 1943. R. CAMPBELL Plant Pat. 608
APPLE TREE
Filed May 5, 1942
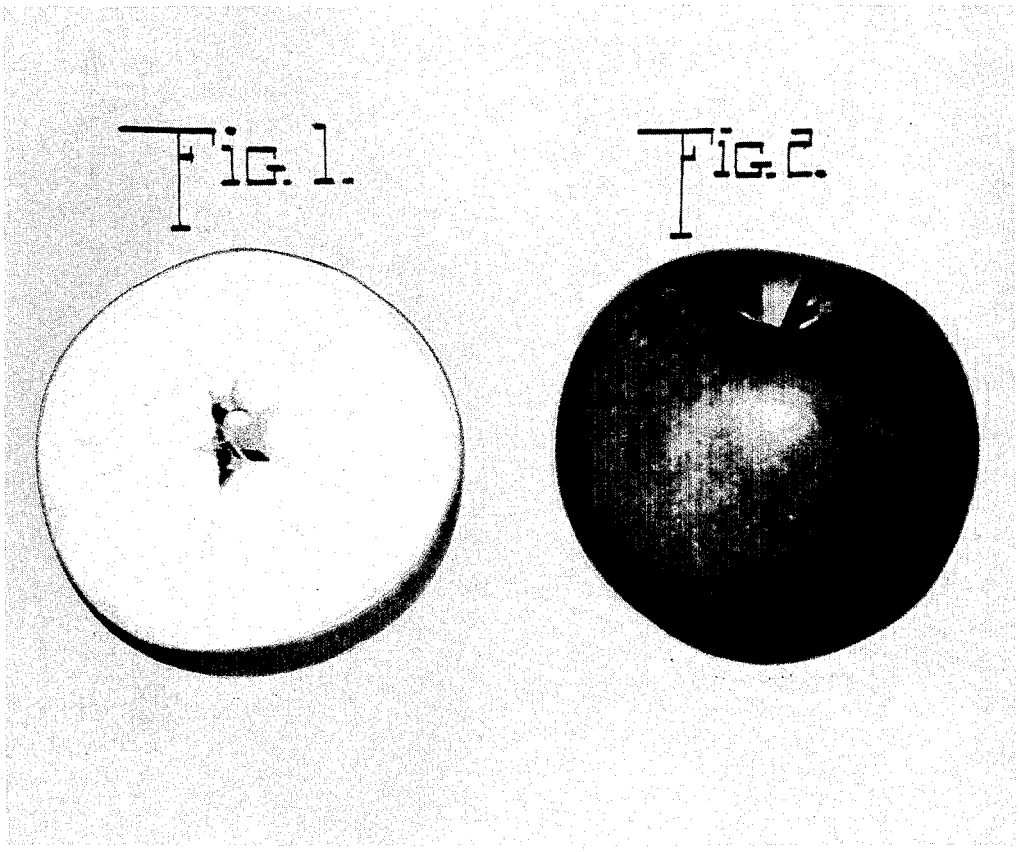
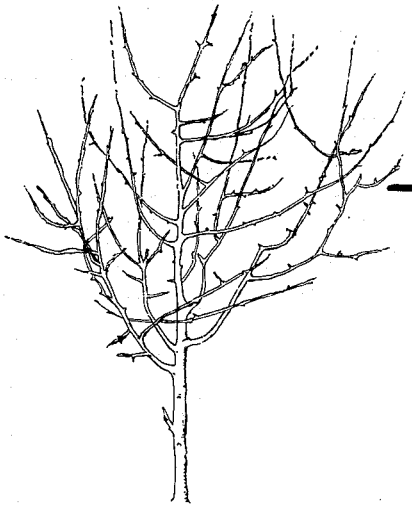
Fig. 3.
INVENTOR
R. Campbell
BY Robb & Robb
ATTORNEYS Patented Nov. 23, 1943

Plant Pat. 608

UNITED STATES PATENT OFFICE

608

APPLE TREE

Robert Campbell, Grand Forks, British Columbia, Canada, assignor to Stark Bro's. Nurseries and Orchards Company, Louisiana, Mo.

Application May 5, 1942, Serial No. 441,851

1 Claim. (Cl. 47—62)

This discovery relates to a new and distinct variety of apple tree originating as a seedling and having as its primary feature its early season of ripening and superior quality of the fruit.

For the purposes of comparison and with reference to the season of ripening, it may be noted that this new variety of apple is of the McIntosh type, but it ripens much earlier than the early McIntosh and just after the well known variety "Yellow Transparent."

As regards the quality of the fruit, it is to be observed that the apple in this case is larger and better in quality than the early McIntosh, and when the fruit has fully matured it has a solid bright red color, and is very firm, crisp and juicy.

A further feature of novelty is found in the fact that by far the higher percentage of the fruit shows a red tinge in the flesh, similar to the depiction in the accompanying illustration.

The tree is very hardy and has a most desirable framework in that most of the branches come out from the trunk at nearly right angles thereto, making a very desirable crotch structure.

In the accompanying illustration, Figure 1 is a view of a cut section of the new apple, showing primarily the red tinge streaks in the flesh; Figure 2 is an elevational view of the apple; and Figure 3 is a detail sketch of a young tree of the new variety showing the habit of growth of the branches at substantially right angles to the trunk.

Asexual reproduction has shown these characteristics to be established. (The following observations are made with reference to specimens of the plant grown in British Columbia.)

The following is a detailed description of the new variety, the color terminology used herein being in accord with Ridgeway's Color Standard and general dictionary meaning:

Tree: Medium in size; vigorous; upright; tall; rapid growing; hardy; productive; regular bearing.

Trunk: Medium stocky; medium smooth.

Branches: Medium thick; smooth; much branching; Brown.

*Lenticels.*—Medium number.

Leaves: Length—4¼ inches; width—2¾ inches. Medium size; medium wide; ovate; taper-pointed; thick; Dark Green; smooth.

*Margin.*—Glandular; finely serrate.

*Petiole.*—Long.

Flowers: Date of first and full bloom, May 1st–May 8th; early compared with other varieties; medium size; Pink.

Fruit:

*Maturity when described.*—Eating ripe in August.

*Size.*—Uniform. Axial diameter, 2¾ inch. Globose; oblate.

*Cavity.*—Symmetrical; acute; pubescent toward apex. Depth, medium; breadth, medium. Markings—circular Russet on some specimens.

*Basin.*—Symmetrical; rounded; even; glabrous. Depth, ⅝ inch; breadth, ¾ inch. Markings—concentric Russeting on some specimens.

*Stem.* — Medium slender; pubescent. Length, ⅞ inch; breadth, $\frac{3}{16}$ inch.

*Calyx.*—Closed; segments persistent; acute. Length, ⅛ inch; imbicate at base; ascending; reflexed. Outer surface—pubescent; inner surface—pubescent.

*Eye.*—Medium size; partially closed.

*Skin.*—Thin; tough; glossy. Dots—obscure; few; small; submerged; circular. Color of dots—Whitish. Distribution of dots—mostly toward caylx end. Ground color—Chalcedony Yellow (Ridgway). Color markings—splashed; dull. Color of markings—Carmine Red splashes. Bloom—scant; scarskin—wanting. General color effect—Yellow Green ground almost entirely covered with Red splashes, striping.

*Flesh.*—Juicy. Color of flesh—white with greenish tint, tinged with Red in cortex near skin; vascular bundles in most specimens. Texture—tender; fine; melting. Flavor—subacid; mild. Aroma—Distinct. Quality—good—best.

*Core.*—Median. Bundle area—medium size; broadly ovate; unsymmetrical; opposite. Halves of area unequal. Bundles—Green, Reddish tinge conspicuous, in two whorls. Alternate bundle—approximate to calyx tube. Core lines — clasping. Carpellary area—distinct; medium size. Calyx tube — pubescent; funnel-form. Stem of funnel—short. Depth of tube to shoulder, $\frac{1}{16}$ inch; entire depth, $\frac{5}{16}$ inch. Styles — present; united toward base; pubescent throughout. Stamens—one; marginal. Auxiliary cavity—wanting. Seed cells—abaxile; open. Cell walls—distant; thin; tough. Longitudinal section—ovate. Surface—fissured. Cross section—broad.

*Seeds.*—Number perfect, 7 to 12; number imperfect, 1 to 3; number in one cell, three. Length, $\frac{3}{16}$ inch; breadth, $\frac{3}{16}$ inch. Form—acute. Color—Chestnut Brown (Ridgway).

Use: Market; dessert.
Keeping quality: Medium.
Resistance to: Insects—good. Disease—medium.

I claim:

A new and distinct variety of Apple tree characterized as to novelty by its early season of ripening, the habit of growth of the branches at substantially right angles to the trunk, and the superior quality of its fruit evidenced by the solid bright red color of the skin and very firm, crisp and juicy character of the flesh, substantially as shown and described.

ROBERT CAMPBELL.